US00PP08171P

United States Patent [19]

VandenBerg

[11] Patent Number: Plant 8,171

[45] Date of Patent: Mar. 9, 1993

[54] CHRYSANTHEMUM PLANT NAMED LYNN

[75] Inventor: Cornelis P. VandenBerg, Salinas, Calif.

[73] Assignee: Yoder Brothers, Inc., Barberton, Ohio

[21] Appl. No.: 741,758

[22] Filed: Aug. 7, 1991

[51] Int. Cl.[5] ..... A01H 5/00

[52] U.S. Cl. ..... Plt./76

[58] Field of Search ..... Plt./76, 81, 82

*Primary Examiner*—Howard J. Locker

*Attorney, Agent, or Firm*—Foley & Lardner

[57] ABSTRACT

A Chrysanthemum plant named Lynn particularly characterized by its flat capitulum form; decorative capitulum type; light purple ray floret color with a distinct darker red-purple center of the flower; diameter across face of capitulum of 51 to 60 mm when fully opened; branching pattern is spreading and prolific, with 7 to 8 breaks after pinch when grown outside under natural daylength in fall flowerings, and 6 breaks when grown in 10 cm pots for spring flowerings; natural season flower date of September 3 to 5 when planting rooted cuttings on June 21 to 23 in Salinas, Calif., and of October 5 to 9 when planting rooted cuttings June 15 to June 18 in Hightstown, N.J.; flowering response of 47 days after rooting in no light/no shade programs in spring in Salinas; plant height, of 25 cm when grown in fall under natural daylength with no growth regulators in New Jersey, and of 15 to 18 cm when grown in 10 cm pots in spring with 0 to 1 application of 2500 ppm B-9 SP; and durable, uniform performance.

3 Drawing Sheets

The present invention comprises a new and distinct cultivar of Chrysanthemum, botanically known as *Dandranthema grandiflora,* and referred to by the cultivar name Lynn.

Lynn, identified as 9349 (88-264001), was originated from a cross made by Cornelis P. VanderBerg in a controlled breeding program in Salinas, Calif., in 1988.

The female parent of Lynn was the cultivar identified as Ginger, disclosed in U.S. Plant Pat. No. 6,403, and described as a flat decorative garden mum with an orange ray floret color and a bronze-red center of the flower; flower diameter of 57 to 64 mm; natural season flower date of August 24 to 28 in Salinas, Calif., and of September 24 to October 1 in Hightstown, N.J.; a flowering response in spring of 43 to 46 days; plant height of 33 to 41 cm in fall natural season flowerings in New Jersey, and of 18 to 20 cm in spring flowerings in 10 cm pots with 1 to 2 applications of 2500 ppm B-9 SP in Salinas.

The male parent of Lynn was an unnamed seedling, identified as 5924 (84M38004) and described as a pink decorative garden mum with many disc florets; flower diameter of 64 mm; natural season flower data of August 24 to September 4 in Salinas, Calif., and of September 24 to October 3 in Hightstown, N.J.; and a plant height of 30 to 33 cm in fall natural season flowerings in New Jersey with no growth regulators. The male parent of Lynn was discarded from the program in May 1988.

Lynn was discovered and selected as one flowering plant within the progeny of the stated cross by Cornelis P. VanderBerg in November 1988, in a controlled environment in Salinas, Calif.

The first act of asexual reproduction of Lynn was accomplished when vegetative cuttings were taken from the initial selection in January 1989 in a controlled environment in Salinas, Calif., by technicians working under supervision of Cornelis P. VanderBerg.

Horticultural examination of controlled flowerings of successive plantings has shown that the unique combination of characteristics as herein disclosed for Lynn are firmly fixed and are retained through successive generations of asexual reproduction.

Lynn has not been observed under all possible environmental conditions. The phenotype may vary somewhat with variations in environment such as temperature, light intensity and daylength, without, however, any variance in the genotype.

The following observations, measurements and comparisons describe plants grown in Salinas, Calif., and in Hightstown, N.J. Rooted cuttings were established in soil and maintained outdoors under the natural temperature and daylength prevailing during June through October. Spring flowerings were conducted in Salinas, Calif. under greenhouse conditions which approximate those generally used in commercial greenhouse practice for small pot spring garden mum production.

The following traits have been repeatedly observed and are determined to be basic characteristics of Lynn, which, in combination, distinguish this Chrysanthemum as a new and distinct cultivar:

1. Flat capitulum form.
2. Decorative capitulum type.
3. Light purple ray floret color with a distinct darker red-purple center of the flower.
4. Diameter across face of capitulum of 51 to 60 mm when fully opened.
5. Branching pattern is spreading and prolific, with 7 to 8 breaks after pinch when grown outside under natural daylength in fall flowerings, and 6 breaks when grown in 10 cm pots for spring flowerings.
6. Natural season flower date of September 3 to 5 when planting rooted cuttings on June 21 to 23 in Salinas, Calif., and of October 5 to 9 when planting rooted cuttings June 15 to June 18 in Hightstown, N.J.
7. Flowering response of 47 days after rooting in no light/no shade programs in spring in Salinas.
8. Plant height of 25 cm when grown in fall under natural daylength with no growth regulators in New Jersey, and of 15 to 18 cm when grown in 10 pots in spring with 0 to 1 application of 2500 ppm B-9 SP.

9. Durable, uniform performance.

The accompanying photographic drawings show typical inflorescence and leaf characteristics of Lynn, with the colors being as nearly true as possible with illustrations of this type.

Sheet 1 is a color photograph of Lynn grown as a pinched spray pot mum with 1 cutting in a 10 cm pot.

Sheet 2 is a black and white photograph of three views of the inflorescence of Lynn.

Sheet 3 is a black and white photograph showing the upper and under sides of the leaves of Lynn at 3 stages of development (mature, intermediate and immature). In sheets 2 and 3 a measuring tape in centimeters has been added.

Of the commercial cultivars known to the inventor, the most similar in comparison to Lynn is the cultivar identified as Debonair, disclosed in U.S. Plant Pat. No. 7,225. Reference is made to attached Chart A, which compares certain characteristics of Lynn to the same characteristics of Debonair.

Similar traits are capitulum form and type and plant height in spring flowering. Lynn has a lighter ray floret color, a smaller diameter of capitulum, a more prolific branching pattern, a later flowering date in natural season fall flowerings, and a shorter plant height in fall flowerings when compared to Debonair.

In the following description color references are made to The Royal Horticultural Society Colour Chart. The color values were determined on plant material grown as a pinched spray pot mum in a 10 cm pot in Salinas, Calif. on Apr. 15, 1991.

Classification:

*Botanical.*—*Dendranthema grandiflora* cv. Lynn.

*Commercial.*—Flat decorative spray pot mum and garden mum.

INFLORESCENCE

A. Capitulum:

*Form.*—Flat.

*Type.*—Decorative.

*Diameter across face.*—51 to 60 mm when fully opened.

B. Corolla of ray florets:

*Color (general tonality from a distance of three meters).*—Light purple, with distinct darker red-purple center of the flower.

*Color (upper surface).*—75B to 75C, with center of flower 70B to 70C.

*Color (under surface).*—75B to 75C.

*Shape.*—Cross section of young ray florets concave, longitudinal section of outer ray florets convex.

C. Corolla of disc florets:

*Color (mature).*—9A.

*Color (immature).*—144C.

D. Reproductive organs:

*Androecium.*—Present on disc florets only; very few, no pollen.

*Gynoecium.*—Present on both ray and disc florets.

PLANT

A. General appearance:

*Height.*—25 cm when grown in fall under natural daylength in New Jersey with no growth regulators, and of 15 to 18 cm when grown in 10 cm pots in spring in Salinas with 0 to 1 application of 2500 ppm B-9 SP.

*Branching pattern.*—Spreading and prolific, with 7 to 8 breaks after pinch when grown outside under natural daylength in fall flowerings, and with 6 breaks when grown in 10 cm pots for spring flowerings.

B. Foliage

*Color (upper surface).*—147A.

*Color (under surface).*—147B.

*Shape.*—See photograph.

CHART A

| CULTIVAR | LYNN | DEBONAIR |
|---|---|---|
| Ray floret color | Light purple with darker center | Purple |
| Capitulum form and type | Flat decorative | Flat decorative |
| Diameter across face of capitulum | 51 to 60 mm | 64 to 70 mm |
| Branching pattern | Spreading and prolific | Spreading |
| Natural season flower date: | | |
| in Salinas, CA | Sept. 3 to 5 | Aug. 26 to 31 |
| in Hightstown | Oct. 5 to 9 | Sept. 24 to 30 |
| Controlled response | 45 to 49 days | 49 to 53 days |
| Plant height: | | |
| in natural season fall | 25 cm | 30 to 38 cm |
| in 10 cm pots spring | 15 to 18 cm | 15 to 20 cm |

COMPARISONS MADE OF PLANTS GROWN AS UNDER NATURAL SEASON OUTDOOR CONDITIONS IN SALINAS, CALIFORNIA AND IN HIGHTSTOWN, NEW JERSEY AND IN SPRING FLOWERING PROGRAMS IN SALINAS, CALIFORNIA

I claim:

1. A new and distinct Chrysanthemum plant named Lynn, as described and illustrated.

* * * * *

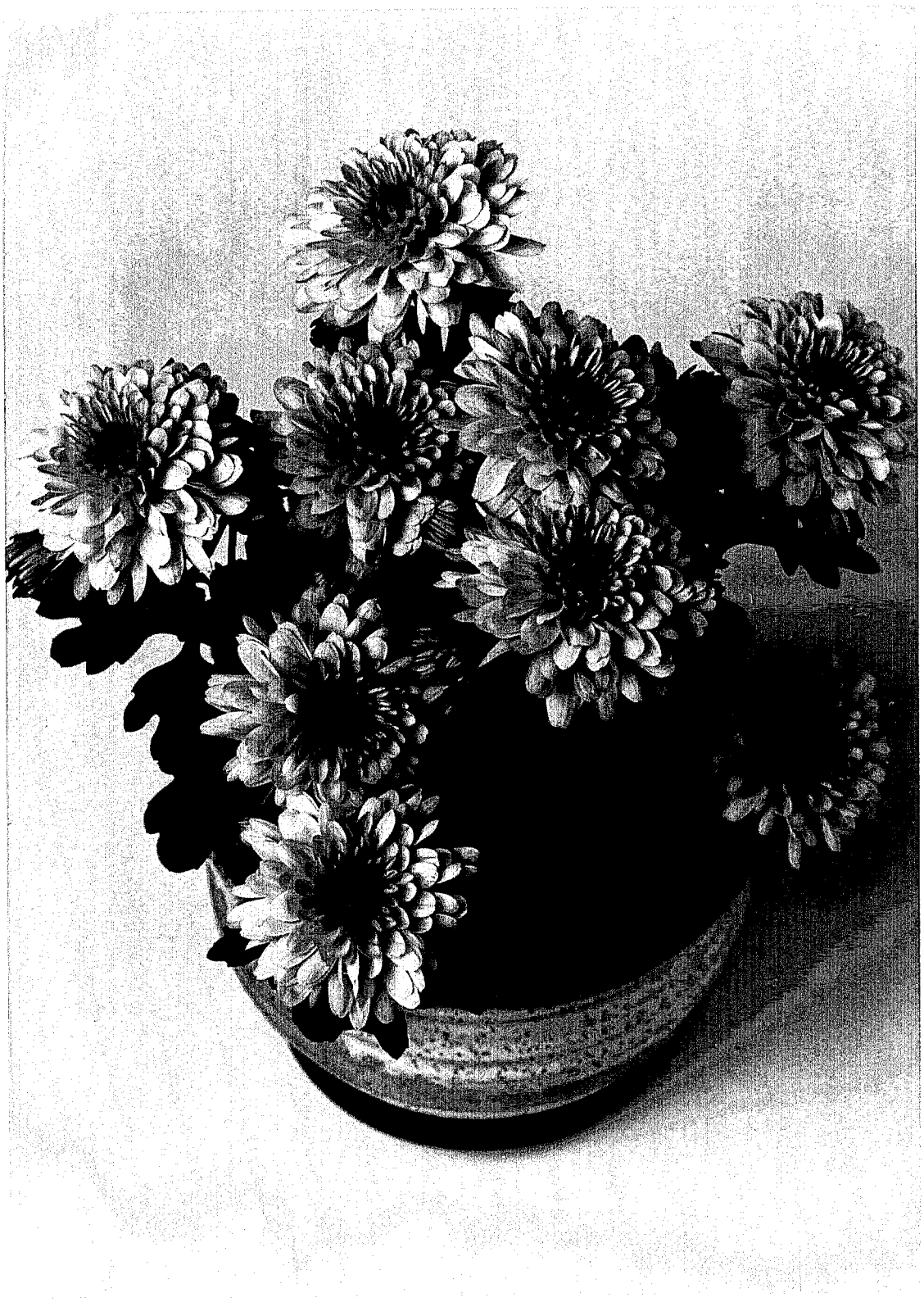

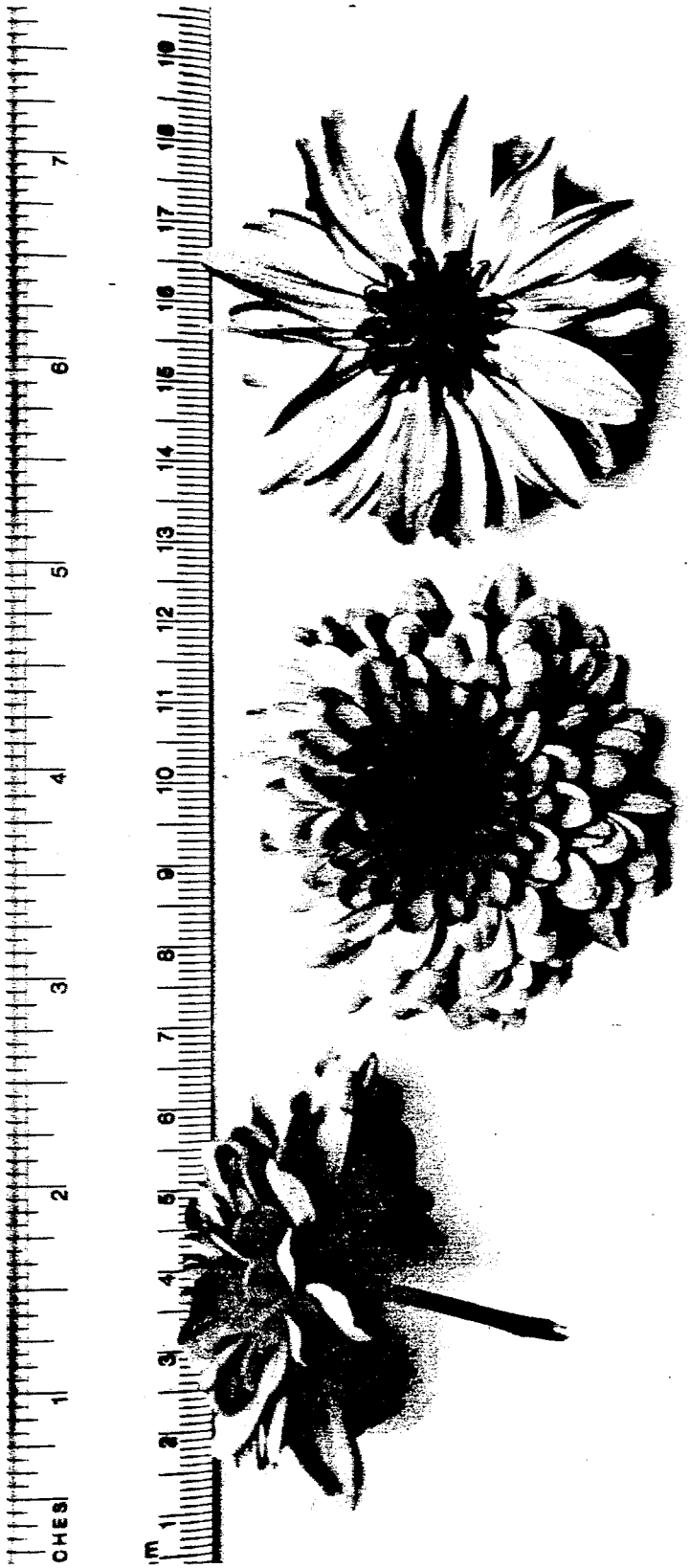
INCHES
1
2
3
4
5
6
7
cm
1
2
3
4
5
6
7
8
9
10
11
12
13
14
15
16
17
18
19

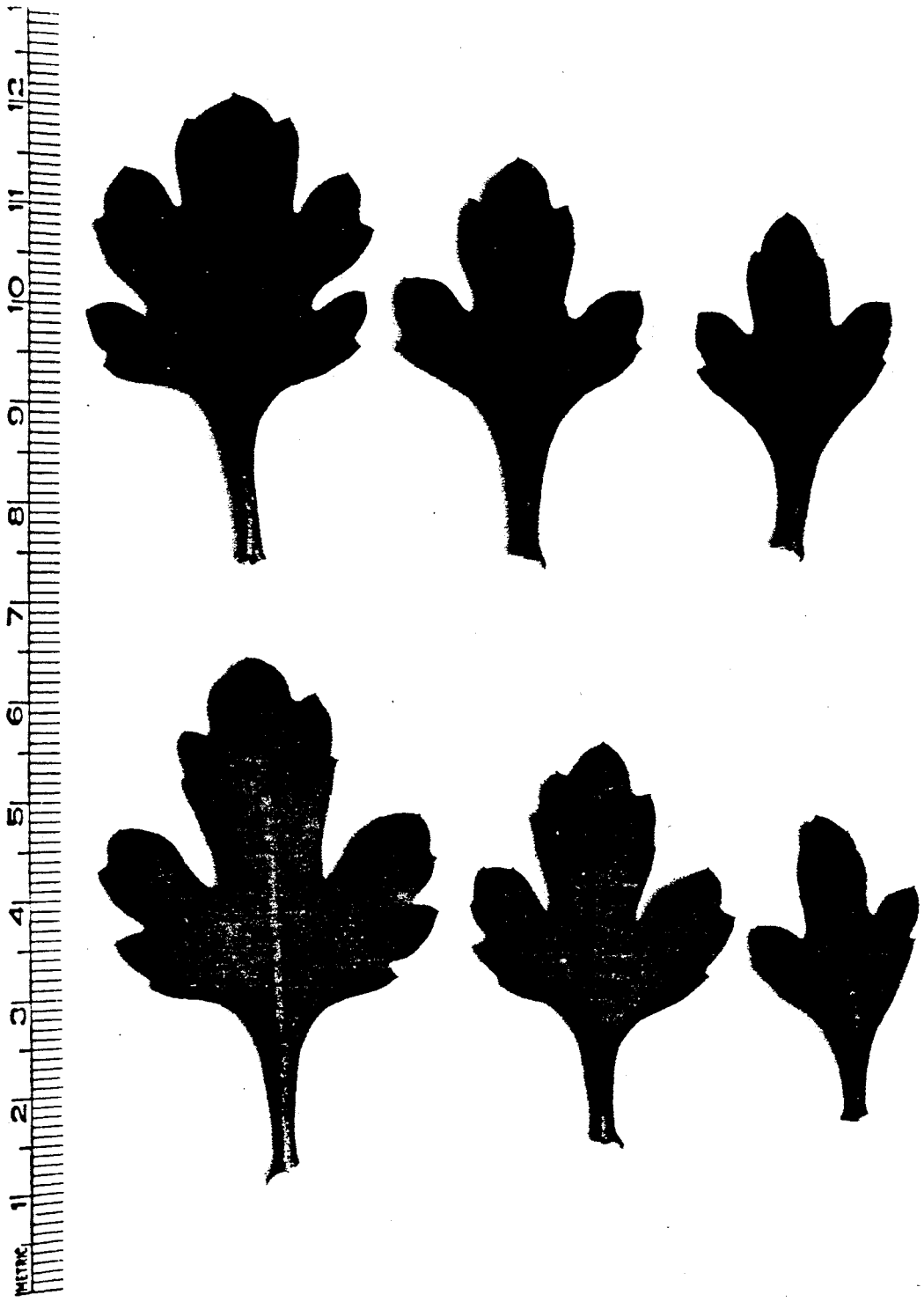
METRIC
1
2
3
4
5
6
7
8
9
10
11
12